United States Patent [19]
Chen

[11] Patent Number: 5,728,173
[45] Date of Patent: Mar. 17, 1998

[54] ARTIFICIAL KNEE JOINT

[76] Inventor: Sen-Jung Chen, No. 236, Sec. 3, Ho-Ping W. Rd., Taipei City, Taiwan

[21] Appl. No.: 637,196

[22] Filed: Apr. 8, 1996

[51] Int. Cl.$^6$ .................................................. A61F 2/64
[52] U.S. Cl. ................................................. 623/44; 623/46
[58] Field of Search ........................... 623/39, 43–46; 602/26

[56] References Cited

U.S. PATENT DOCUMENTS

| | | | |
|---|---|---|---|
| 2,537,351 | 1/1951 | Johnson et al. | 623/44 X |
| 5,545,232 | 8/1996 | Van de Veen | 623/39 |

FOREIGN PATENT DOCUMENTS

| | | | |
|---|---|---|---|
| 1109153 | 8/1984 | U.S.S.R. | 623/44 |
| 9222267 | 12/1992 | WIPO | 623/44 |

OTHER PUBLICATIONS

Geri–Lite 4 Bar Stability 3–4 Knee, RK–4300, Design by Proteor (Brochure), pp. 12.1 and 12.2.

*Primary Examiner*—David H. Willse
*Attorney, Agent, or Firm*—Knobbe, Martens, Olson & Bear, LLP

[57] ABSTRACT

An artificial knee joint includes a shank formed with a pair of upwardly extending first lugs and a pair of radially extending second lugs, and a thigh support formed with a pair of downwardly extending third lugs which are connected pivotally to the first lugs. A connector has a first portion which extends between and which is mounted pivotally to the third lugs, a second portion which extends from the first portion and which extends between the first lugs, and a connecting portion formed at a junction of the first and second portions. A biasing unit on the shank biases the second portion of the connector upwardly. The connecting portion of the connector extends between and is connected pivotally to a spaced pair of pivot blocks on an upper end of an actuating member. The actuating member further has a lower end which extends between and which is connected pivotally to the second lugs. Each of a pair of damping units is provided on a respective one of the first lugs so as to bias the pivot blocks, respectively.

3 Claims, 4 Drawing Sheets

5,728,173

ARTIFICIAL KNEE JOINT

BACKGROUND OF THE INVENTION

1. Field of the Invention

The invention relates to an artificial knee joint, more particularly to an artificial knee joint which enables the user to walk steadily along a gradually sloping path.

2. Description of the Related Art

Referring to FIG. 1, a conventional artificial knee joint 1 by Century XXII Innovations Inc. of the United States is shown to include a thigh support 10, a shank 11 and a link assembly 12 which interconnects pivotally the thigh support 10 and the shank 11. A resilient cushioning member 13 is provided on a top end of the shank 11. In use, when first and second link members 121, 122 of the link assembly 12 lie along a substantially straight line, such as when the artificial knee joint 1 is extended to support the user on the ground, the second link member 122 abuts against the cushioning member 13, thereby cushioning any shock due to impact between the ground and an artificial leg which incorporates the knee joint 1. However, when the knee joint 1 is used to support the user on a sloping path, the knee joint 1 is seldom extended fully, thus resulting in an ineffective cushioning action by the cushioning member 13 which may cause the user to lose his balance.

Referring to FIG. 2, another conventional artificial knee joint 2 by Otto Bock of Germany is shown to similarly include a thigh support 20, a shank 21 and a link assembly 22 which interconnects pivotally the thigh support 20 and the shank 21. A hydraulic cylinder 23 is connected to the thigh support 20 and the link assembly 22 and serves to provide a restoring force for the knee joint 2. An inclined cushioning rod 222 is connected pivotally to a lower end of a link member 221 of the link assembly 22, and abuts against a resilient cushioning member 25 which is disposed on the shank 21. If the knee joint 2 is bent slightly, such as when supporting the user on a gradually sloping path, the link member 221 causes the cushioning rod 222 to compress the cushioning member 25, thus enabling the user to walk steadily on the sloping path.

One of the drawbacks of the conventional artificial knee joint 2 resides in that the cushioning force provided by the cushioning member 25 cannot be adjusted to suit the user's needs. In addition, the cushioning member 25 requires an axial support rod 251 which extends therethrough to ensure proper operation of the cushioning member 25. The space allocated for movement of the support rod 251 when the cushioning member 25 is compressed increases the size of the knee joint 2. As a result, the knee joint 2 is larger than a natural knee joint. Thus, the conventional artificial knee joint 2 does not adhere with the common practice of making artificial limbs or joints appear as natural as possible.

SUMMARY OF THE INVENTION

The main object of the present invention is to provide an artificial knee joint which enables the user to walk steadily along a gradually sloping path.

Another object of the present invention is to provide an artificial knee joint with a cushioning effect that can be adjusted so as to suit the user's needs.

A further object of the present invention is to provide an artificial knee joint which can correspond with a natural knee joint in size.

According to the present invention, an artificial knee joint comprises:

a shank formed with a spaced pair of upwardly extending first lugs and a spaced pair of radially extending second lugs;

a thigh support formed with a spaced pair of downwardly extending third lugs;

a link assembly including: a pair of linking members, each of which has a first end portion connected pivotally to one of the third lugs and a second end portion connected pivotally to one of the first lugs; a connector having an inclined first portion with a lower section and an upper section that extends between and that is mounted pivotally to the third lugs, a second portion which extends horizontally from the lower section of the first portion and which extends between the first lugs, and a connecting portion formed at a junction of the first and second portions; and a biasing unit provided on the shank for biasing the second portion of the connector upwardly; and a cushioning unit including: an actuating member having an upper end formed with a spaced pair of pivot blocks, the connecting portion of the connector extending between and being connected pivotally to the pivot blocks, the actuating member further having a lower end which extends between and which is connected pivotally to the second lugs; and a pair of damping units, each of which is provided on a respective one of the first lugs, each of the pivot blocks having a rear side which abuts against a respective one of the damping units.

Preferably, each of the first lugs has a front side, a rear side and a bore which extends from the front side to the rear side and which has a diameter-reduced front end and an internally threaded rear end. Each of the damping units is provided in the bore of the respective one of the first lugs and includes a pin member disposed movably in the bore, a stopper mounted threadedly in the rear end of the bore, and a spring disposed between the pin member and the stopper for biasing the pin member away from the stopper. The pin member has a tip which extends through the front end of the bore and an enlarged base to guard against removal of the pin member from the bore via the front end of the bore. The tip of the pin member abuts against the rear side of the respective one of the pivot blocks.

BRIEF DESCRIPTION OF THE DRAWINGS

Other features and advantages of the present invention will become apparent in the following detailed description of the preferred embodiment with reference to the accompanying drawings, of which.

DETAILED DESCRIPTION OF THE PREFERRED EMBODIMENT

Figure 1:
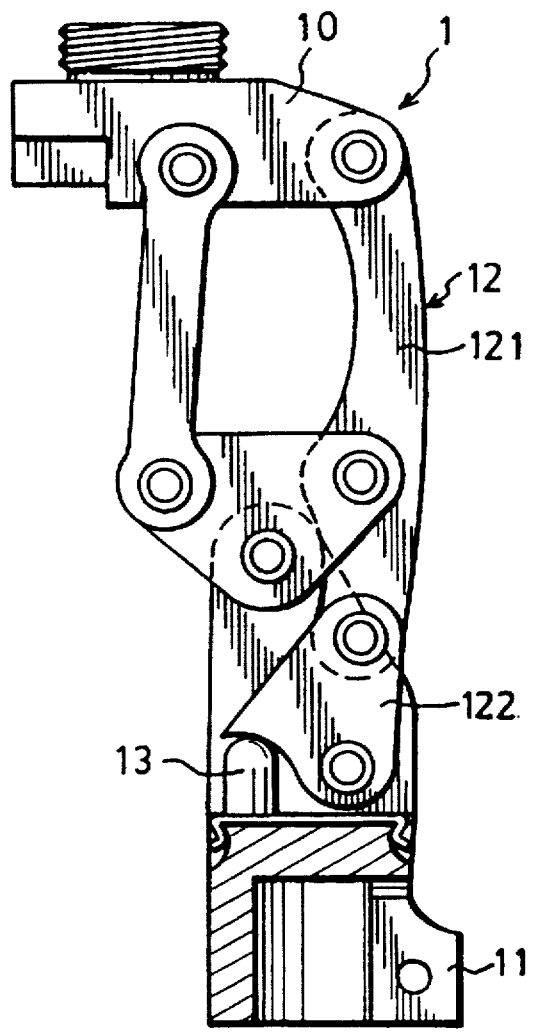
FIG. 1 is a schematic view of a conventional artificial knee joint.
Figure 2:
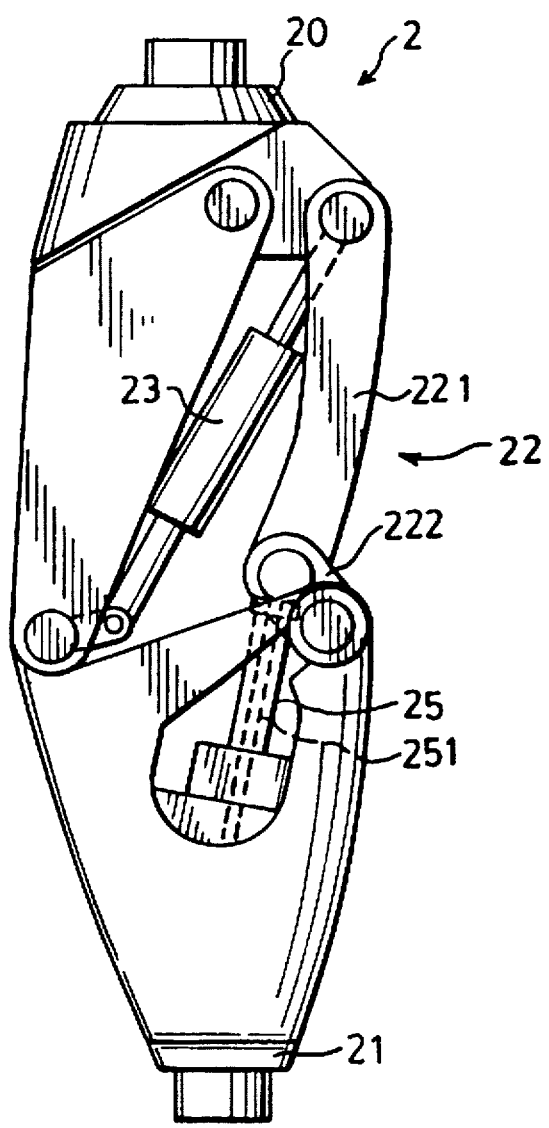
FIG. 2 is a schematic view of another conventional artificial knee joint.
Figure 3:
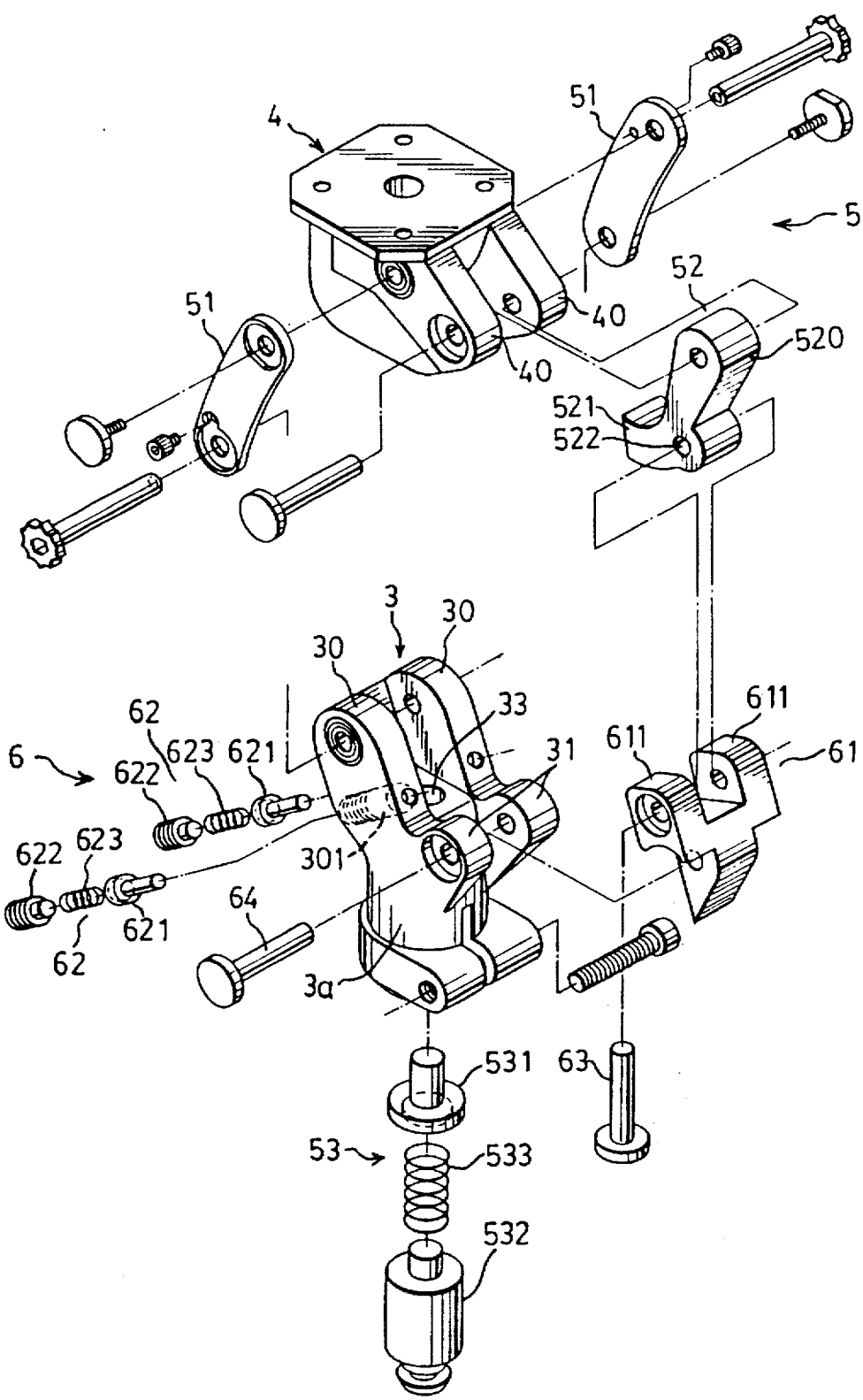
FIG. 3 is an exploded view of the preferred embodiment of an artificial knee joint according to the present invention.
Figure 5:
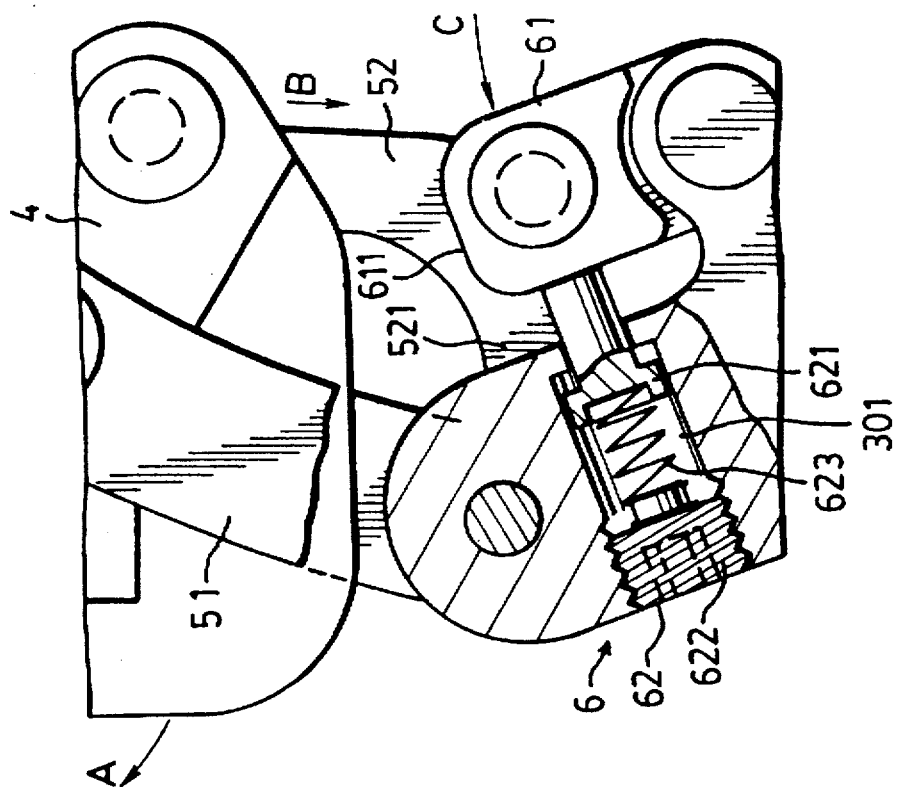
FIG. 5 is an enlarged, partly sectional, schematic view which illustrates operation of a cushioning unit of the preferred embodiment.
Figure 4:
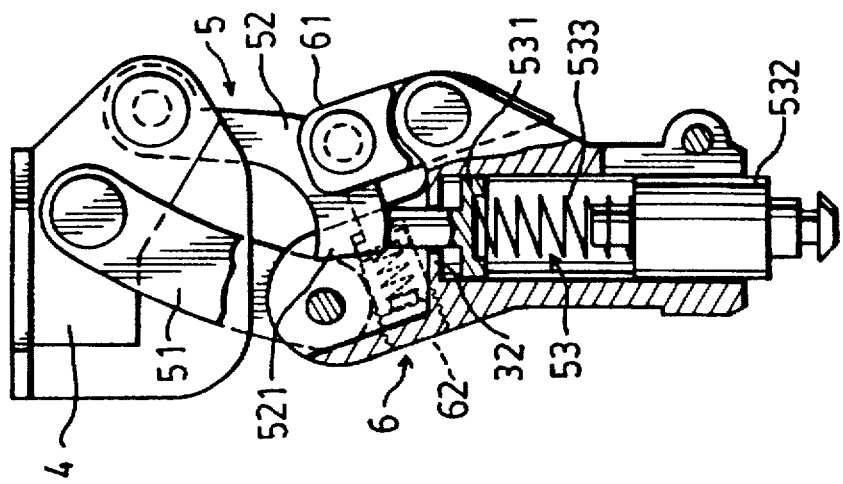
FIG. 4 is a schematic, partly sectional view illustrating the assembly of the preferred embodiment.

Referring to FIGS. 3 to 5, the preferred embodiment of an artificial knee joint according to the present invention is shown to comprise a shank 3, a thigh support 4, a link assembly 5, and a cushioning unit 6.

The shank 3 includes a tubular body 3a formed with a spaced pair of upwardly extending first lugs 30 and a spaced pair of radially extending second lugs 31. Each of the first lugs 30 has a front side, a rear side and a bore 301 which extends from the front side to the rear side. The bore 301 has a diameter-reduced front end and an internally threaded rear end. The tubular body 3a further has a top end formed with a radial inward flange 32 that confines a through-hole 33.

The thigh support 4 is formed with a spaced pair of downwardly extending third lugs 40.

The link assembly 5 connects pivotally the shank 3 and the thigh support 4, and includes a pair of linking members 51, a connector 52 and a biasing unit 53. Each of the linking members 51 has a first end portion connected pivotally to one of the third lugs 40 and a second end portion connected pivotally to one of the first lugs 30. The biasing unit 53 is provided in the tubular body 3a and includes a pin member 531 disposed movably in the tubular body 3a, a stopper 532 mounted in a bottom end of the tubular body 3a, and a spring 533 disposed between the pin member 531 and the stopper 532 for biasing the pin member 531 away from the stopper 532. The pin member 531 has a tip which extends through the through-hole 33 in the top end of the tubular body 3a, and an enlarged base to guard against removal of the pin member 531 from the tubular body 3a via the through-hole 33. The connector 52 has an inclined first portion 520 with an upper section that extends between and that is mounted pivotally to the third lugs 40, and a second portion 521 which extends horizontally from a lower section of the first portion 520 and which extends between the first lugs 30. The second portion 521 has a bottom side that abuts against the tip of the pin member 531 of the biasing unit 53. The connector 52 further has a connecting portion 522 formed at a junction of the first and second portions 521, 522.

The cushioning unit 6 includes an actuating member 61 and a pair of damping units 62. The actuating member 61 has an upper end formed with a spaced pair of pivot blocks 611. The connecting portion 522 of the connector 52 extends between and is connected pivotally to the pivot blocks 611 by means of a pivot pin 63. The actuating member 61 further has a lower end which extends between and which is connected pivotally to the second lugs 31 by means of a pivot pin 64. Each of the damping units 62 is provided in the bore 301 of a respective one of the first lugs 30 and includes a pin member 621 disposed movably in the bore 301, a stopper 622 mounted threadedly in the rear end of the bore 301, and a spring 623 disposed between the pin member 621 and the stopper 622 for biasing the pin member 621 away from the stopper 622. The pin member 621 has a tip which extends through the front end of the bore 301 and an enlarged base to guard against removal of the pin member 621 from the bore 301 via the diameter-reduced front end of the latter. The tip of the pin member 621 abuts against the rear side of a respective one of the pivot blocks 611.

Referring to FIGS. 4 and 5, in use, when the thigh support 4 pivots in the direction indicated by the arrow (A), the linking members 51 and the connector 52 pivot accordingly. The second portion 521 of the connector 52 compresses the biasing unit 53, which serves to provide a restoring force for restoring the knee joint to a fully extended position. When an artificial leg which incorporates the preferred embodiment supports the user on the ground, a force (B) is applied on the connector 52, thereby causing the actuating member 61 to pivot in the direction indicated by the arrow (C). At this time, the actuating member 61 compresses the damping units 62, as shown by the arrow (D), thus cushioning the shock due to impact between the artificial leg and the ground even when the ground slopes gradually downward. Therefore, the artificial knee joint of this invention enables the user to walk steadily along a sloping path. In addition, in view of the threaded engagement between the stoppers 622 of the damping units 62 and the bores 301 in the first lugs 30, the degree of compression of the springs 623 can be adjusted to adjust correspondingly the cushioning force that is provided by the cushioning unit 6 in accordance with the user's needs. Moreover, since the artificial knee joint of this invention does not require a relatively large space for movement of an axial support rod, which space is required in the conventional artificial knee joint 2 described beforehand, the artificial knee joint of this invention can correspond with a natural knee joint in size. The objects of the present invention are thus met.

While the present invention has been described in connection with what is considered the most practical and preferred embodiment, it is understood that this invention is not limited to the disclosed embodiment but is intended to cover various arrangements included within the spirit and scope of the broadest interpretation so as to encompass all such modifications and equivalent arrangements.

I claim:

1. An artificial knee joint, comprising:

a shank formed with a spaced pair of upwardly extending first lugs and a spaced pair of radially extending second lugs;

a thigh support formed with a spaced pair of downwardly extending third lugs;

a link assembly including: a pair of linking members, each of which has a first end portion connected pivotally to one of said third lugs and a second end portion connected pivotally to one of said first lugs; a connector having an inclined first portion with a lower section and an upper section that extends between and that is mounted pivotally to said third lugs, a second portion which extends horizontally from said lower section of said first portion and which extends between said first lugs, and a connecting portion formed at a junction of said first and second portions; and a biasing unit provided on said shank for biasing said second portion of said connector upwardly; and a cushioning unit including: an actuating member having an upper end formed with a spaced pair of pivot blocks, said connecting portion of said connector extending between and being connected pivotally to said pivot blocks, said actuating member further having a lower end which extends between and which is connected pivotally to said second lugs; and a pair of damping units, each of which is provided on a respective one of said first lugs, each of said pivot blocks having a rear side which abuts against a respective one of said damping units.

2. The artificial knee joint as claimed in claim 1, wherein:

each of said first lugs has a front side, a rear side and a bore which extends from said front side to said rear side, said bore having a diameter-reduced front end and an internally threaded rear end; and each of said damping units is provided in said bore of the respective one of said first lugs and includes a pin member disposed movably in said bore, a stopper mounted threadedly in said rear end of said bore, and a spring disposed between said pin member and said stopper for biasing said pin member away from said stopper, said pin member having a tip which extends through said front end of said bore and an enlarged base to guard against removal of said pin member from said bore via said front end of said bore, said tip of said pin member abutting against said rear side of the respective one of said pivot blocks.

3. The artificial knee joint as claimed in claim 1, wherein:

said shank includes a tubular body which has a top end formed with a radial inward flange that confines a through-hole, and a bottom end; and said biasing unit is provided in said tubular body and includes a pin member disposed movably in said tubular body, a stopper mounted in said bottom end of said tubular body, and a spring disposed between said pin member and said stopper for biasing said pin member away from said stopper, said pin member having a tip which extends through said through-hole in said top end of said tubular body, and an enlarged base to guard against removal of said pin member from said tubular body via said through-hole, said second portion of said connector having a bottom side that abuts against said tip of said pin member.

* * * * *